United States Patent
Peyman

(10) Patent No.: US 6,436,092 B1
(45) Date of Patent: Aug. 20, 2002

(54) ADJUSTABLE UNIVERSAL IMPLANT BLANK FOR MODIFYING CORNEAL CURVATURE AND METHODS OF MODIFYING CORNEAL CURVATURE THEREWITH

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 0 days.

(21) Appl. No.: 09/532,516

(22) Filed: Mar. 21, 2000

(51) Int. Cl.$^7$ .............................................. A61B 18/18
(52) U.S. Cl. .......................... 606/5; 623/5.11; 351/159
(58) Field of Search ..................... 606/4, 5; 351/159, 351/160 R, 161, 162, 160 H, 177; 128/898; 623/4.1, 5.11, 5.12, 5.13, 5.16

(56) References Cited

U.S. PATENT DOCUMENTS

| | | | |
|---|---|---|---|
| 4,563,565 A | * 1/1986 | Kampfer et al. | 351/160 R |
| 4,676,790 A | * 6/1987 | Kern | 623/5.11 |
| 4,718,418 A | 1/1988 | L'Esperance | 128/303 |
| 4,840,175 A | 6/1989 | Peyman | 128/303.1 |
| 4,976,709 A | * 12/1990 | Sand | 606/5 |
| 4,994,058 A | 2/1991 | Raven et al. | 606/5 |
| 5,196,027 A | 3/1993 | Thompson et al. | 623/5 |
| 5,336,261 A | 8/1994 | Barrett et al. | 623/5 |
| 5,647,865 A | * 7/1997 | Swinger | 606/5 |
| 5,722,971 A | 3/1998 | Peyman | 606/5 |
| 5,824,086 A | * 10/1998 | Silvestrini | 623/5.11 |
| 5,919,185 A | 7/1999 | Peyman | 606/5 |

OTHER PUBLICATIONS

Karin R. Sletten, MD et al.; Experimental Science, "An In Vivo Model of Femtosecond Laser Intrastromal Refractive Surgery", Ophthalmic Surgery and Lasers, Nov./Dec. 1999, vol. 30, No. 9, pp. 742–749.

Griffith et al.; "Functional Human Corneal Equivalents Constructed from Cell Lines", Science, vol. 286, Dec. 10, 1999, pp. 2169–2172.

(List continued on next page.)

Primary Examiner—David O. Reip
Assistant Examiner—Julian W. Woo
(74) Attorney, Agent, or Firm—Roylance,Abrams,Berdo & Goodman, L.L.P.

(57) ABSTRACT

A universally sized blank made of organic or synthetic material, or a hybrid combination of an organic and synthetic material, that can be placed on an exposed inner surface of a live cornea and, if desired, ablated with a laser beam to be altered to a particular shape. The blank further includes material which can increase the volume of the blank when exposed to a particular energy, and another material which can decrease or shrink the volume of the blank when exposed to a particular type of energy. A flap-like portion of the live cornea is removed to expose an inner surface of the cornea, and the blank is positioned on the exposed inner surface of the eye. If desired, a laser beam is directed onto certain portions of the blank that are selected based on the type of ametropic condition (i.e., myopia, hyperopia or astigmatism) of the eye needing correction, so that the laser beam ablates those portions and thus reshapes the blank. The laser beam can also be directed onto certain portions of the laser surface of the cornea to ablate those surfaces of the cornea. The flap-like portion of the cornea is repositioned over the remaining portion of the blank, so that the remaining portion of the blank influences the shape of the reattached flap-like portion of the cornea and thus modifies the curvature of the cornea. The appropriate energy can be irradiated onto the ablated or unablated blank, to increase or decrease the volumes of portions of the blank, as appropriate, to modify or further modify the curvature of the cornea to more precisely correct the vision disorder. Alternatively, the blank can include a plurality of sections, which can be removed through a small incision in the cornea to adjust the correction factor.

60 Claims, 14 Drawing Sheets

OTHER PUBLICATIONS

Yamauchi et al.; "Cultivation of fibroblast cells on keratin-coated substrata", Polymers for Tissue Engineering, pp. 329–340, VSP 1998.

Ijima et al.; "Formation of a spherical multicellular aggregate (spheroid) of animal cells in the pores of polyurethane foam as a cell culture substratum and its application to a hybrid artificial liver", Polymers for Tissue Engineering, pp. 273–286, VSP 1998.

Cao et al.; "Comparative study of the use of poly(glycolic acid), calcium alginate and pluronics in the engineering of autologous porcine cartilage", Polymers for Tissue Engineering, pp. 315–327, VSP 1998.

Jose I. Barraquer, M.D., "Keratomileusis and keratophakia in the surgical correction of aphakia", pp. 270–289, published before Mar. 21, 2000.

* cited by examiner

ADJUSTABLE UNIVERSAL IMPLANT BLANK FOR MODIFYING CORNEAL CURVATURE AND METHODS OF MODIFYING CORNEAL CURVATURE THEREWITH

CROSS-REFERENCE TO RELATED PATENT AND APPLICATIONS

Related subject matter is disclosed in U.S. Pat. Nos. 5,919,185, 5,722,971 and 4,840,175, in a application entitled "A Universal Implant Blank for Modifying Corneal Curvature and Methods of Modifying Corneal Curvature Therewith", Ser. No. 09/260,591, filed Mar. 2, 1999; now U.S. Pat. No. 6,063,073, and in a application entitled "Instrastromal Corneal Modification", Ser. No. 09/260,571, filed Mar. 2, 1999, now U.S. Pat. No. 6,280,470. The entire contents of each of the above-referenced patent applications and patents are incorporated herein by reference.

BACKGROUND OF THE INVENTION

1. Field of the Invention

The present invention relates to an adjustable universal blank which is used to modify the curvature of a live cornea when implanted therein. The blank includes a synthetic or organic material which is adaptable for ablation by a laser beam while the blank is supported on an exposed surface of the cornea, and which further can cause area of the blank to increase or decrease in volume when that area is irradiated with energy such as light of a particular wavelength, microwaves, or thermal energy.

2. Description of the Related Art

A normal emetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia up to 6 diopters, or in eyes suffering from hypermetropic, hyperopic or astigmatic conditions which are not very severe, that method is ineffective in correcting vision in eyes suffering from sever forms of ametropia. For example, known optical methods are typically ineffective in correcting high myopia of 6 diopters or greater, and are also ineffective in correcting severe astigmatism and severe forms of hypermetropia or hyperopia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then reattached to the main portion of the live cornea. Hence, it is intended that the reshaped cornea will change the position at which the light entering the eye through the cut portion is focused, so that hopefully the light is focused on the retina, thus remedying the ametropic condition.

The myopic keratomileusis technique is known to be effective in curing myopic conditions within a range of 6 to 18 diopters. However, the technique is impractical because it employs very complicated and time consuming freezing, cutting and thawing processes. Furthermore, the technique is ineffective in correcting myopic conditions greater than 18 diopters.

Keratophakia is another known surgical technique for correcting sever ametropic conditions of the eye by altering the shape of the eye's cornea. In this technique an artificial organic or synthetic lens is implanted inside the cornea to thereby alter the shape of the cornea and thus change its refractive power. Accordingly, as with the myopic keratomileusis technique, it is desirable that the shape of the cornea be altered to a degree allowing light entering the eye to be focused correctly on the retina.

However, the keratophakia technique is impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea. Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M.D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, referenced above, which emit pulsed ultraviolet radiation, can be used to decompose or photoablate tissue in the live cornea so as to reshape the cornea.

Specifically, a laser surgical technique known as laser in situ keratomycosis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outbulging (eklasia), this technique is not especially effective in correcting very high myopia. That is, a typical live cornea is on average about 500 microns thick. The laser ablation technique requires that at least about 200 microns of the corneal stroma remain after the ablation is completed so that instability and outbulging does not occur. Hence, this procedure typically cannot be effectively used to correct high myopia of greater than 15 diopters because in order to reshape the cornea to the degree necessary to alter its refractive power so as to sufficiently correct the focusing of the eye, too much of the cornea would need to be ablated.

Accordingly, as described in U.S. Pat. No. 5,919,185 cited above, another technique has been developed by the present inventor which involves placing a universally sized blank made of organic or synthetic material on an exposed inner surface of a live cornea, and ablating the blank with a laser beam to alter the blank to a particular shape. Specifically, a flap-like portion of the live cornea is removed to expose an inner surface of the cornea, and the blank is positioned on the exposed inner surface of the eye. A laser beam is directed onto certain portions of the blank that are selected based on the type of ametropic condition (i.e., myopia, hyperopia or astigmatism) of the eye needing correction, so that the laser beam ablates those portions and thus reshapes the blank. The laser beam can also be directed onto certain portions of the laser surface of the cornea to ablate those surfaces of the cornea. The flap-like portion of the cornea is repositioned over the remaining portion of the blank, so that the remaining portion of the blank influences the shape of the reattached flap-like portion of the cornea and thus modifies the curvature of the cornea.

This technique is effective in modifying the curvature of the cornea to correct the types of severe vision disorders described above. However, after the initial procedure has been performed, it is at times necessary to further modify the size and shape of the implanted blank to make fine adjustments to its refractive power, and thus further improve the patient's vision. In this event, it is necessary to reopen the flap in the cornea, and either further ablate the blank on the exposed corneal surface, or replace the blank with another blank having a size and shape more suitable to correct the vision disorder. This additional surgery can create the risk of damage to the patient's eye, and cause further patient discomfort.

A need therefore exists for improved methods for further modifying an implanted blank to better correct very severe ametropic conditions.

SUMMARY OF THE INVENTION

An object of the present invention is to provide a system and method for adjusting, without ablation, the size and shape of a blank that has been implanted into a live cornea to modify corneal curvature to thus correct severe ametropic conditions.

Another object of the invention is to provide a blank that can be implanted into a live cornea to modify corneal curvature to thus correct severe ametropic conditions, and which is modifiable without ablation.

A further object of the invention is to provide a blank including a material that increases the volume of the blank in response to energy, and which further includes a material that shrinks or decreases the volume of the blank in response to energy, without ablating the blank.

These and other objects are substantially obtained by providing a universally sized blank made of organic material, synthetic material, or a combination of organic and synthetic material, that can be placed on an exposed inner surface of a live cornea and ablated with a laser beam to be altered to a particular shape. The universally sized blank can be porous to allow oxygen and nutrients to pass there through. Also, the blank can be made from living cells such as a donor cornea of a human eye (e.g., as taken from an eye bank), or can be taken from a cultured cornea. The blank can further include material which increases the volume of the blank in response to energy, and another material that shrinks or decreases the volume of the blank in response to energy.

A flap-like portion of the live cornea is removed to expose the inner surface of the cornea. The blank is positioned on the exposed inner surface of the cornea and, if desired, a laser beam is directed onto certain portions of the blank to ablate those portions and thus reshape the blank based on the type of ametropic condition (i.e., myopia, hyperopia or astigmatism) of the eye needing correction. The flap-like portion of the cornea is then repositioned over the remaining portion of the blank, so that the remaining portion of the blank influences the shape of the reattached flap-like portion of the cornea, thus modifying the curvature of the surface of the cornea. Whether or not the blank has been ablated, the appropriate energy can be applied to the blank, to increase or decrease the volume of the blank, as desired, to further alter the curvature of the cornea to more precisely correct the vision disorder.

Alternatively, the blank include multiple sections. Certain of these sections can be removed or added, as appropriate, to modify the curvature of the surface of the cornea by the necessary amount to correct the vision disorder.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which.

DETAILED DESCRIPTION OF THE PREFERRED EMBODIMENTS

Figure 1:
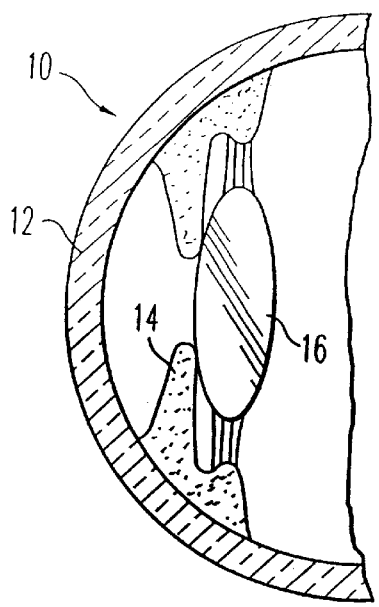
FIG. 1 is a side elevational view in section taken through the center of an eye showing the cornea, pupil and lens.

FIG. 1 is a side elevational view in section taken through the center of an eye 10 which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

Figure 2:
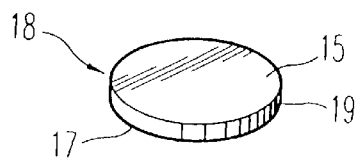
FIG. 2 is a perspective view of an embodiment of a universal blank according to the present invention.
Figure 3:
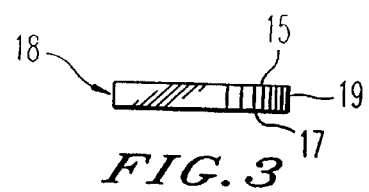
FIG. 3 is a front elevational view of the embodiment shown in FIG. 2.
Figure 4:
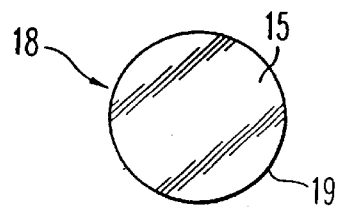
FIG. 4 is a top elevational view of the embodiment shown in FIG. 2.

A universal blank 18 according to an embodiment of the present invention is illustrated in FIGS. 2–4. As shown, the universal blank according to this embodiment is disk-shaped and has a uniform or substantially uniform thickness throughout, as illustrated specifically in FIG. 3. Specifically, the blank 18 has a first planar or substantially planar surface 15, a second planar or substantially planar surface 17, and a periphery 19. The surfaces 15 and 17 are arranged parallel or substantially parallel to each other with the periphery 19 being perpendicular or substantially perpendicular to one or both surfaces 15 and 17. Of course, the surfaces 15 and 17 and the periphery 19 need not be uniform but could have recesses, projections, raised portions, or any variation in shape and texture. Preferably, the universal blank 18 has a diameter of about 1 mm to about 10 mm and a thickness of between about 20 to about 500 microns, or up to several millimeters. Of course, the diameter and thickness of the disk-shaped universal blank 18 can be of any practical size as would be appreciated by one skilled in the art. Furthermore, the universal blank need not be disk-shaped although it is preferred as shown in the embodiment of FIGS. 2–4, but can be frusto-conical, oval, square, rectangle, or any practical shape as would be readily appreciated by one skilled in the art.

The blank 18 is preferably made of synthetic material, organic material, or a combination of both synthetic and organic material, that permits all or substantially all light having a wavelength in the visible spectrum to pass through, but absorbs all or substantially all light having a wavelength in a laser light spectrum. For example, the blank 18 can be made of collagen, copolymer collagen, polyethylene oxide, polypropylene, polyproledine or hydrogel, or cross-linked organic material such as collagen, hyaluronic acid, mucopolysacoharide or glycoprotein, to name a few. The blank 18 is porous to allow oxygen and nutrients to pass therethrough. Also, the blank 18 can be made from a donor cornea of a human eye, or can be taken from a cultured cornea. However, the blank 18 is not limited to those materials, and can be made of any suitable material, such as those disclosed in U.S. Pat. No. 4,994,058 to Raven et al., U.S. Pat. No. 4,718,418 to L'Esperance, U.S. Pat. No. 5,336,261 to Barrett et al., U.S. Pat. No. 4,840,175 to Peyman, and a publication by Jose I. Barraquer, M.D. entitled "Keratomileusis and Keratophakia in the Surgical Correction of Aphakia", the disclosures of which are hereby incorporated by reference herein.

The blank 18 can also be made of a hybrid material, which can be a combination of organic material and one or more polymers, such as those described above. The blank 18 can further be made of or include a tissue matrix comprising a collagen-chondroitin sulfate substrate, which is cross-linked with 0.02% to 0.04% glutaraldehyde and then treated with glylcine to remove unbound glutaraldehyde, as described in a publication by May Griffith et al. entitled "Functional Human Corneal Equivalents Constructed from Cell Lines", Science, Vol. 286, Dec. 10, 1999. The blank 18 can further include fibroblast cells on keratincoated substrata, as described in an article by Kiyoshi Yamauchi et al. entitled "Cultivation of Fibroblast Cells on Keratin-Coated Substrata", Polymers for Tissue Engineering, 1998, pp. 329–340, or a spherical multicellular aggregate of animal cells in the pores of polyurethane foam as described in an article by Hiroyuki Ijima et al. entitled "Formation of a Spherical Multicellular Aggregate (Spheroid) of Animal Cells in the Pores of Polyurethane Foam as a Cell Culture Substream and its Application to a Hybrid Artificial Liver", Polymers for Tissue Engineering, 1998, pp. 273–286. Also, the blank 18 can include polyglycolic acid, calcium alginate and pluronics in autologous porcine cartilage as described in an article by Yilin Cao et al. entitled "Comparative Study of the Use of Poly(glycolic acid), Calcium Alginate and Pluronics in the Engineering of Autologous Porcine Cartilage", Polymers for Tissue Engineering, 1998, pp. 315–327.

Furthermore, for reasons discussed in detail below, the blank 18 can include a silicone polymer which includes loose monomers that are responsive to light within a certain wavelength range, such as the short ultraviolet wavelength range or the blue light wavelength range. In response to the light, the monomers become aggravated, and cross-linking occurs which increases the volume of the area of the blank 18 being irradiated with the light.

The blank 18 can also include a polymer comprising a polycarbonate or acrylic material containing a dye or dyes manufactured, for example, by Centex Company. The dye or dyes absorb light within a certain wavelength range, such as the infrared wavelength range, which causes slight melting or softening of the material. This melting or softening results in a decrease or flattening of the irradiated area of the blank 18, and thus reduces the volume of that area for purposes discussed in more detail below.

Figure 5:
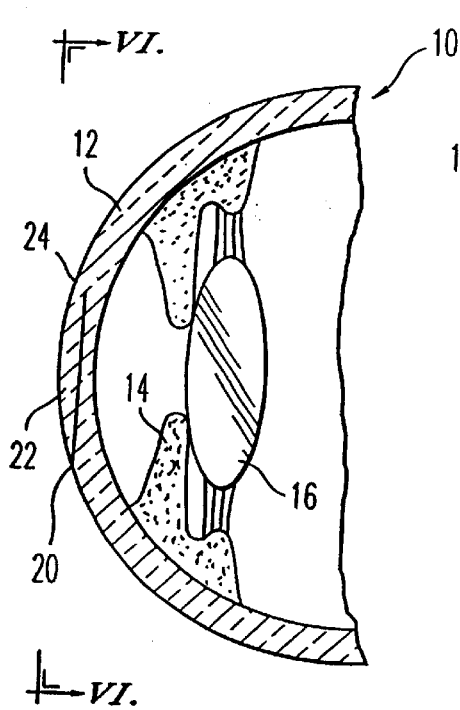
FIG. 5 is a side elevational view in section taken through the center of an eye showing formation of a flap-like structure at the front of the cornea.

The blank 18 is configured to be placed directly on an exposed inner surface of the cornea of the eye. In order to expose this inner surface of the cornea of the eye, a thin layer of the live cornea must be removed. To remove the layer of the cornea, a procedure is performed in which, for example, an incision 20 is made in the front portion of the cornea, as shown in FIG. 5. This incision 20 is made so as to separate thin layer 22 of the cornea from the remaining portion of the cornea 12. The incision can be made with a scalpel, keratome, excimer laser, or any type of surgical cutting instrument known to one skilled in the art. The layer 22 can also be separated from the surface of the live cornea by any other method which may not involve making an actual incision in the cornea as may be appreciated by one skilled in the art.

Figure 6:
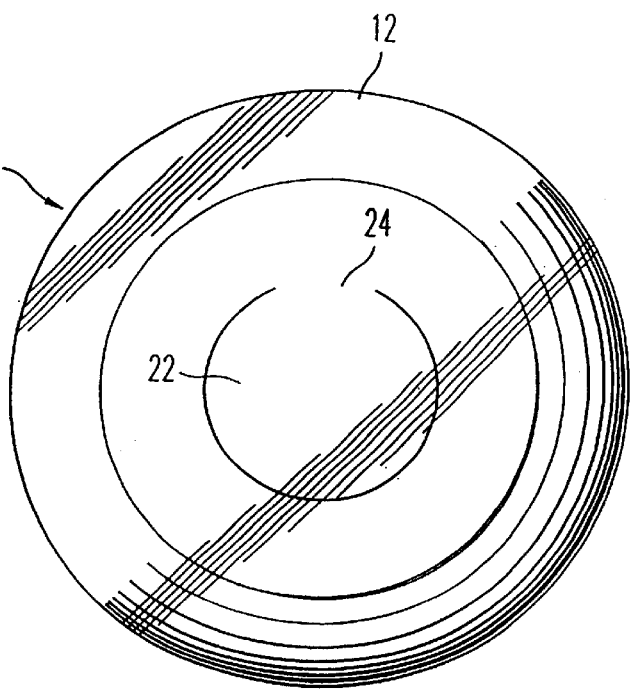
FIG. 6 is a front elevational view of the cornea and flap-like structure as taken along lines VI—VI in FIG. 5.
Figure 7:
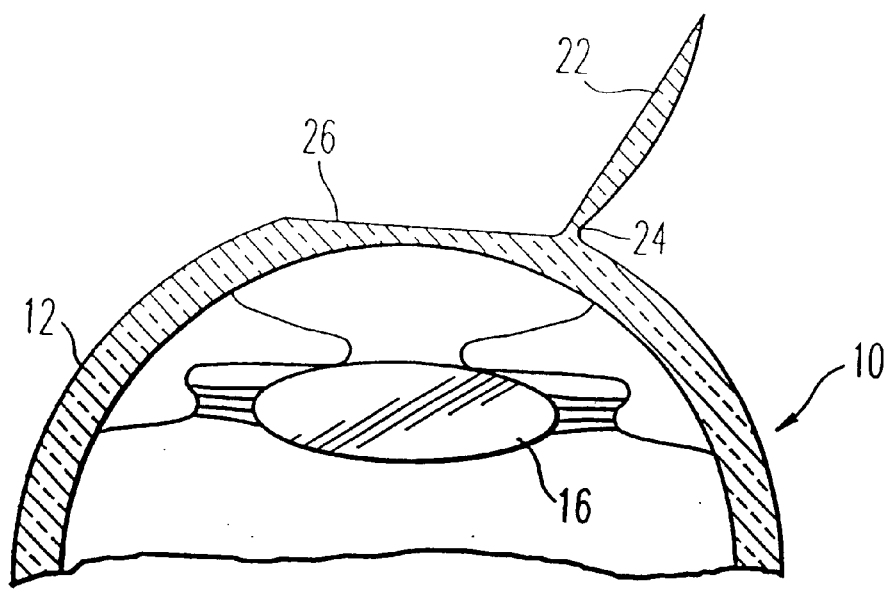
FIG. 7 is a side elevational view in section taken through the center of an eye and showing the flap-like section positioned to expose an inner surface of the cornea.

The layer 22 of the cornea can be completely removed from the remaining portion of the cornea 12. However, as shown in FIGS. 5 and 6, it is preferable that the layer 22 of the cornea remain attached to the main portion of the live cornea 12 by an attaching or hinging portion 24 Accordingly, as shown in FIG. 7, the layer 22 of the cornea is formed as a flap-like layer that is pivotally moveable about the attaching portion 24 to expose an inner surface 26 of the cornea. The layer 22 typically can be of any practical thickness, for example, 160 microns, and can have a uniform thickness throughout or a varying thickness.

The universal blank 18 is then used to modify the curvature of the cornea in the following manner.

Figure 8:
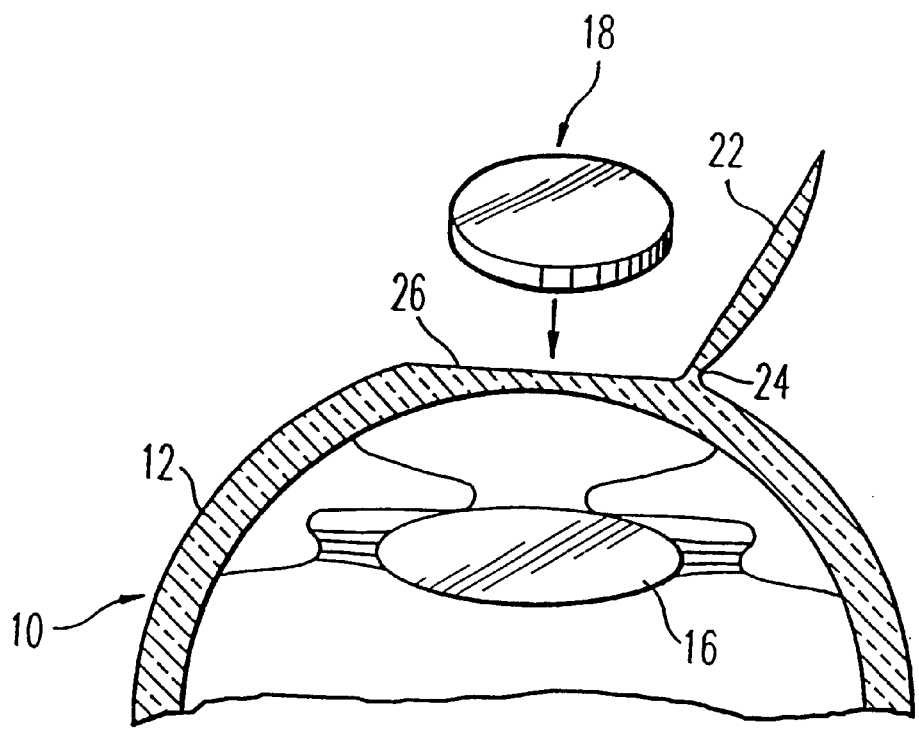
FIG. 8 is an enlarged side elevational view in section taken through the center of an eye and showing placement of the embodiment of the universal blank shown in FIG. 2 on the exposed surface of the cornea.
Figure 9:
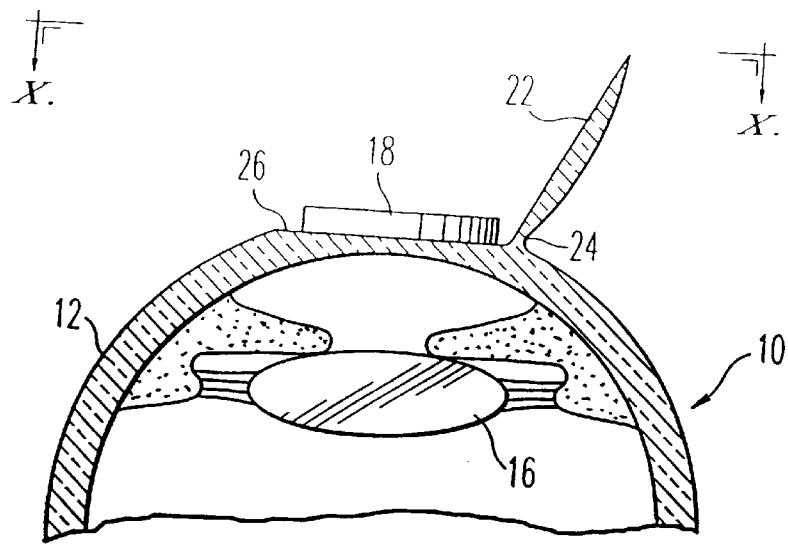
FIG. 9 is an enlarged side elevational view in section taken through the center of an eye and illustrating the universal blank shown in FIG. 2 positioned on the exposed surface of the cornea.
Figure 10:
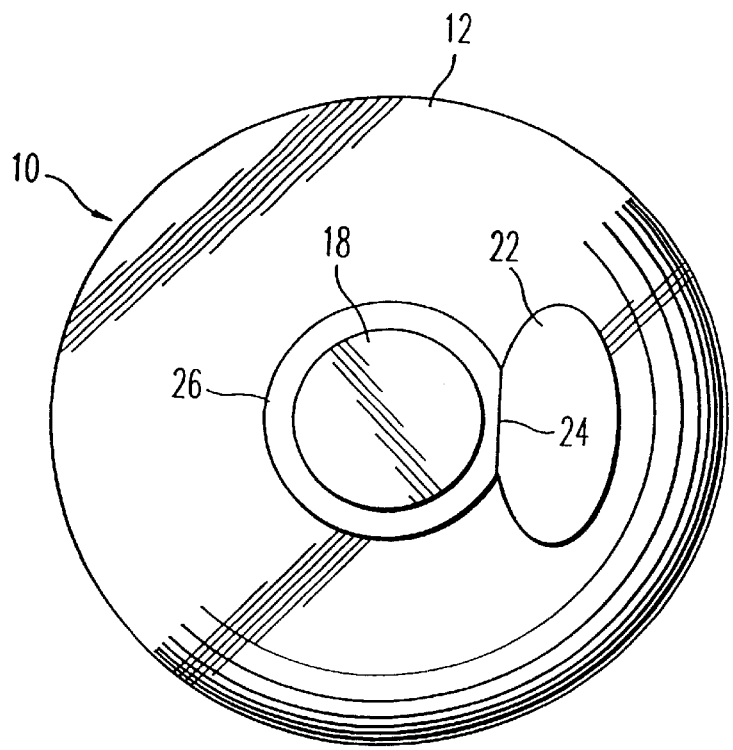
FIG. 10 is a front elevational view of the cornea with the universal blank present on the exposed surface thereof as taken along lines X—X in FIG. 9.
Figure 11:
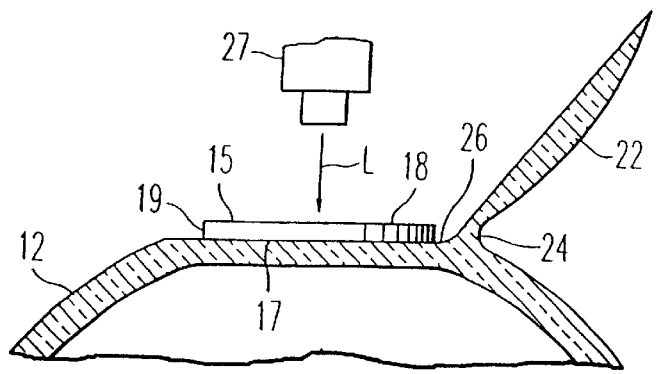
FIG. 11 is an enlarged side elevational view in section taken through the center of the eye showing the cornea and the irradiation of a laser beam on the universal blank positioned on the exposed surface of the cornea.

As shown in FIGS. 8 and 9, the flap-like layer 22 is positioned so as to expose the inner surface 26 of the cornea. The blank 18 is then positioned on the exposed surface of the cornea at a position deemed suitable by the person performing the cornea modifying technique. Typically, as shown in FIG. 10, the blank 18 is positioned centrally or substantially centrally on the exposed surface 26 with the central longitudinal axis of the blank substantially coincident with the central optical axis of the eye. Of course, the blank 18 need not be positioned centrally on the exposed surface 26 as shown, but rather, its central longitudinal axis can be offset from the central optical axis of the eye.

Once positioned on the exposed surface 26 of the cornea 12, the shape of the universal blank can be modified sufficiently to influence the shape of the flap-like layer 22 and to thus change the refractive power of the flap-like layer sufficiently to correct the abnormality of the eye 10. Generally, every 10 micron change in curvature of the cornea will change the refractive power of the cornea by 1 diopter.

For example, as shown in FIGS. 11–14, a laser beam L is directed to the first upper surface 15 of the blank 18 that is opposite to the second lower surface 17 of the blank 18 that is supported on the exposed surface 26 of the cornea 12. The laser beam L can be emitted from any type of laser 27 typically used in eye surgery methods, such as an excimer laser 27 or the like as described in U.S. Pat. No. 4,840,175.

Figure 12:
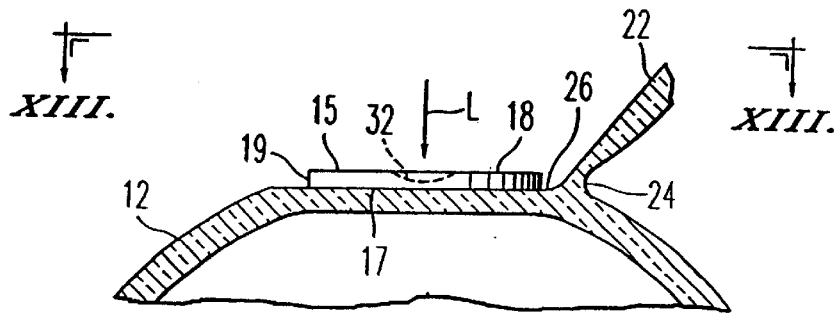
FIG. 12 illustrates ablation of the center of the universal blank by the laser beam.

As shown in FIG. 12, the laser beam L will begin to ablate or erode an area 32 of the blank 18 to which the laser beam is directed. Alternatively, the blank 18 can be made to the appropriate shape prior to placing it on the exposed surface of the cornea. Again, the area of the blank 18 to which the laser beam L is directed and which is ablated is selected to remedy a specific type of abnormality from which the eye is suffering.

Figure 13:
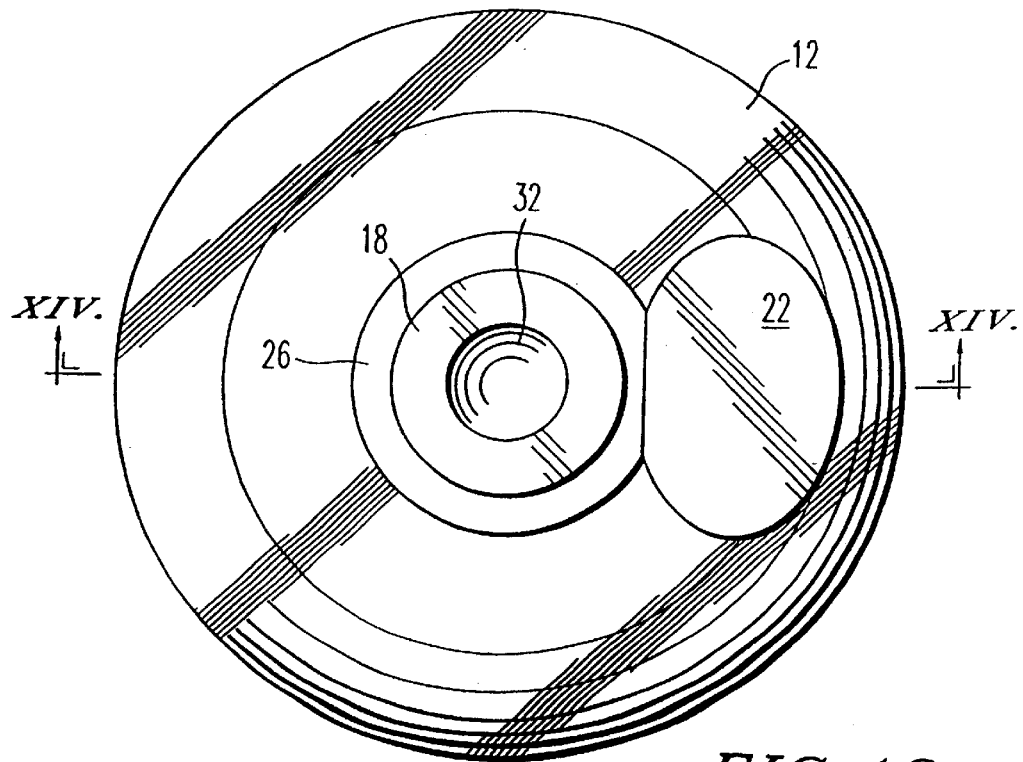
FIG. 13 is a reduced front elevational view of the ablated universal blank taken along lines XIII—XIII in FIG. 12.

For example, if the blank is being used to correct a myopic condition, the laser beam L will be directed toward a central area 32 of the blank 18 so as to ablate that central area 32. As shown in FIG. 13, for example, the blank 18 is diskshaped, and the area 32 that is ablated is circular in top plan view and is at least initially in the form of a substantially hemispheric recess. Of course, the shape of the ablated area can be any desired shape necessary to effect correction of the particular abnormality of the eye.

As stated previously, the blank 18 is made of a material that will absorb all or substantially all light having a wavelength within a laser light spectrum. Therefore, when the laser beam L is irradiated onto the blank 18, none or substantially none of the laser beam will pass through the blank 18 to ablate any portion of the cornea 12. However, as also previously stated, the material of the blank 18 will allow all or substantially all light having a wavelength within the visible light spectrum to pass therethrough.

Figure 14:
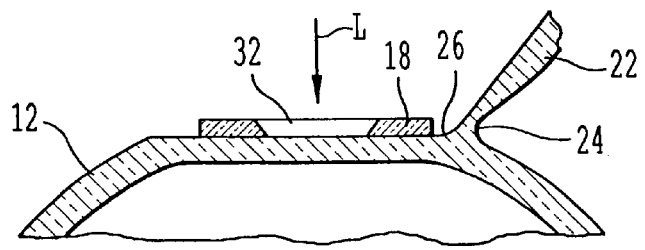
FIG. 14 is an enlarged cross-sectional view of the blank and cornea as taken along lines XIV—XIV in FIG. 13.

Hence, as shown in FIG. 14, the laser beam L can be directed to the blank 18 until the ablated central area 32 becomes a hole with a frustoconical wall which passes entirely through the blank 18 to expose a portion 34 of the surface 26 of the cornea 12. Of course, the hole can have a cylindrically or substantially cylindrically shaped wall, or any other shape as would be formed by the laser beam L. As shown in FIG. 14, none or essentially none of the surface 26 of the cornea has been ablated by the laser beam.

Figure 15:
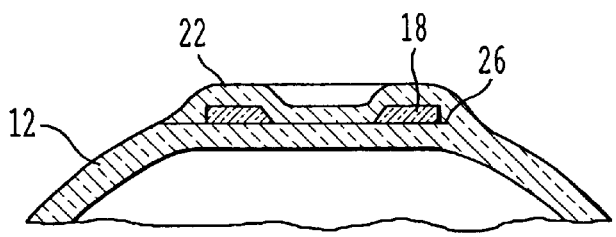
FIG. 15 is a side elevational view in section taken through the center of the eye showing the cornea and the flap-like portion reattached over the exposed surface of the cornea and the remaining portion of the ablated universal blank shown in FIG. 14.

After the laser ablation process has been completed, the flap-like layer 22 of the cornea is repositioned over the remaining portion of the blank 18 and the surface 26 of the cornea 12 as shown, for example, in FIG. 15. As illustrated, the shape of the remaining portion of the blank 18 will influence the shape of the flap-like layer 22 when the flap-like layer is repositioned over the remaining portion of the blank 18 and surface 26 of the cornea 12. Hence, the refractive power of this flap-like layer 22 will be changed due to this change in shape. The flap-like layer 22 can be reattached to the cornea 12 by any known techniques such as suturing, tissue adhesive, or the like.

Because the material of the blank 18 is transparent or essentially transparent to light having a wavelength within the visible light spectrum, visible light will pass through the remaining portion to the blank 18 and enter the eye 12. However, because the reshaped flap-like layer 22 has a different refractive power, the flap-like layer 22 will refract the light passing therethrough differently than prior to the reshaping. Therefore, in cooperation with the lens 16 (see FIG. 1), this reshaped layer 22 will focus the light in the appropriate manner on the retina, thus correcting the ametropic condition of the eye.

It is further noted that the laser 27 can be used to reduce the overall thickness of the blank 18 prior to shaping the blank. For instance, the blank 18 can initially be about 500 microns thick for ease of handling. Then, once the blank 18 is positioned on the exposed inner surface of the cornea in the manner described above, the inner beam L can be directed to the upper surface 15 of the blank so as to reduce the overall thickness of the blank 18 as desired. Hence, a 500 micron thick blank can be reduced, for example, to about 100 microns or any suitable thickness by the laser beam L before the laser beam L is used to sculpt the blank 18 to a particular shape as shown, for example, in FIGS. 11–15.

Additionally, based on the severity of the abnormality from which the eye is suffering, it may be determined that the surface of the cornea must be reshaped more extensively, or in other manners, which are described in U.S. Pat. No. 5,919,185 referenced above.

Once the universal blank 18 has been implanted and ablated as discussed above, and the layer 22 has been replaced, the patient's vision can then be monitored as the cornea 12 heals. If it is then determined that further adjustment should be made to curvature of the cornea 12, the size and shape of the blank 18 can be adjusted without surgically separating the layer 22 from the remainder of the cornea 12. That is, as discussed above, the blank 18 can include certain monomers which, when irradiated with light within a certain wavelength range (e.g., blue or ultraviolet light), become agitated and cross-link, which causes the blank 18 to increase in size at the area of the irradiation. Furthermore, the blank 18 can include a material comprising dyes as discussed above which will absorb laser light (continuous or pulsed) of a particular wavelength (e.g., infrared light) that is irradiated onto an area of the blank 18 to cause melting of the blank 18 in that irradiated area, without ablating the irradiated area. It is noted that when the pulsed laser light is focused properly to a location within the blank, it can disrupt and thus shrink or melt the blank without the need of an absorbent dye. An example of such a laser is a laser which emits nano-second pulses, pico-second pulses or femtosecond pulses of laser light. Furthermore, laser light having a wavelength that is absorbed by water, or other types of energy such as microwave radiation, radio frequency radiation, or thermal energy, can be used to cause shrinkage in the blank without ablating the blank 18 and without lifting the layer 22. In any of the above methods, the additional shaping of the blank 18 is performed substantially without causing damage to the layer 22.

Figure 16:
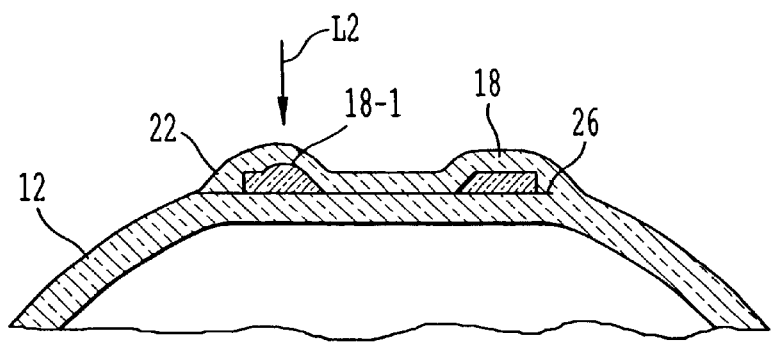
FIG. 16 is a side elevational view in section taken through the center of the eye showing the cornea and the flap-like portion reattached over the exposed surface of the cornea and the remaining portion of the ablated universal blank shown in FIG. 14, with the remaining portion of the blank further being irradiated with light of a particular wavelength to increase the volume of the irradiated area.

As shown in FIG. 16, an area 18-1 is irradiated by laser light which passes through the layer 22. The laser light L2 has a wavelength, such as long ultraviolet wavelength or light within the blue light spectrum, to aggravate the monomers, which causes a cross-linking effect that increases the volume of the blank 18 in the area 18-1 being irradiated. Hence, as the thickness of the blank 18 increases in the area 18-1, this increase thickness changes the curvature of the flap as shown, thus changing the refractive power of the cornea to a degree necessary to correct the remainder of the vision disorder that was not corrected by the ablated blank 18.

Figure 17:
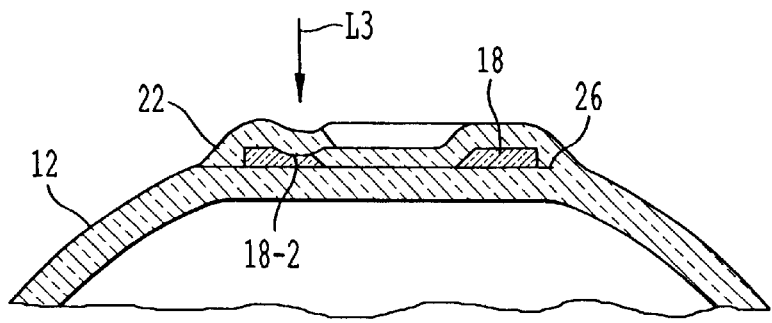
FIG. 17 is a side elevational view in section taken through the center of the eye showing the cornea and the flap-like portion reattached over the exposed surface of the cornea and the remaining portion of the ablated universal blank shown in FIG. 14, with the remaining portion of the blank further being irradiated with energy to decrease the volume of the irradiated area.

Alternatively, as shown in FIG. 17, an area 18-2 of the blank 18 is irradiated with energy L3, such as infrared light, laser light, microwave energy, radio frequency energy, or heat applied by a probe (not shown), to cause the area 18-2 of the blank to shrink or, in other words, reduce in volume. This shrinkage occurs with or without further ablation of the blank 18 and without damage to the layer 22 or other portion of the cornea 12. Accordingly, the shrinkage causes a change in the shape of the layer 22 over the area 18-2, and thus changes the refractive power of the layer 22 to further correct for the remaining vision disorder that was not fully corrected by the ablated blank 18.

Figure 18:
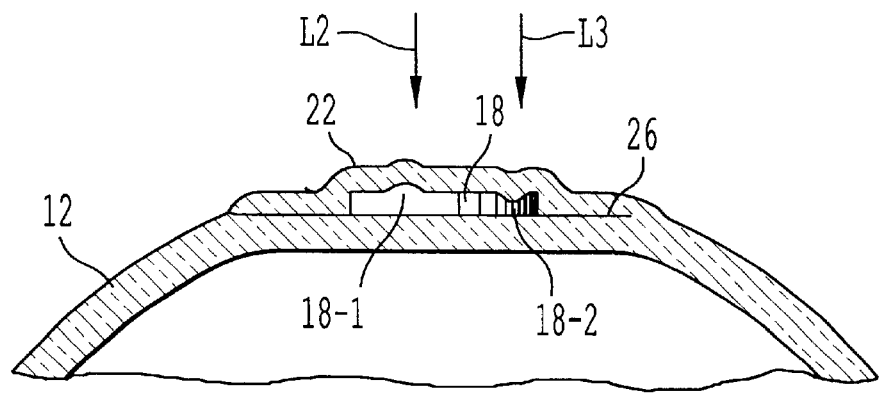
FIG. 18 is a side elevational view in section taken through the center of the eye showing the cornea and the flap-like portion reattached over the exposed surface of the cornea and an unablated universal blank, with the blank further being irradiated with light and energy and respective first and second areas to increase and decrease the volumes, respectively, of the irradiated areas.

It is further noted that as shown in FIG. 18, the blank 18 can be implanted in the cornea under the layer 22 without ablation. Then, in a manner similar to that described above, the particular light or energy can be applied to the areas of the blank, for example, areas 18-1 and 18-2, to create an increase or decrease in volume, as appropriate. This increase or decrease in volume of the areas 18-1 and 18-2 of blank 18 changes the shape of the layer 22, and thus changes the overall refractive power of the layer 22 in a manner similar to that discussed above with regard to the ablated blank 18. Accordingly, this change of shape corrects the vision disorder, as necessary, without the need for ablating the blank 18.

Figure 19A:
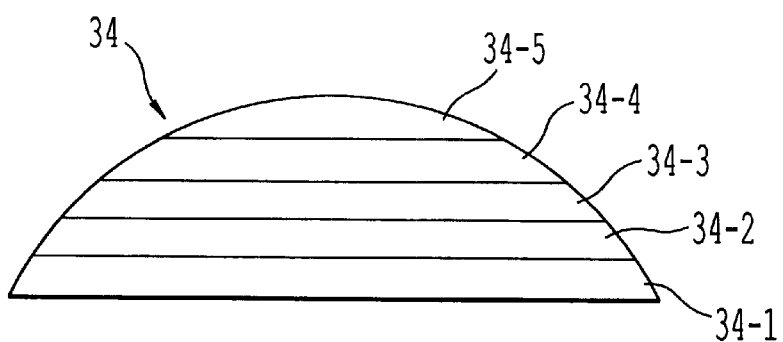
FIG. 19A and 19B are side views of multi-layer blanks according to other embodiments of the present invention.
Figure 19B:
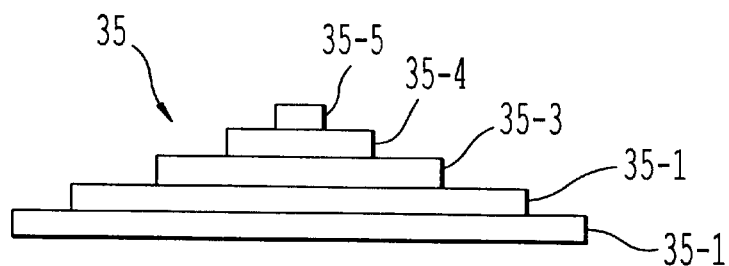
Figure 20:
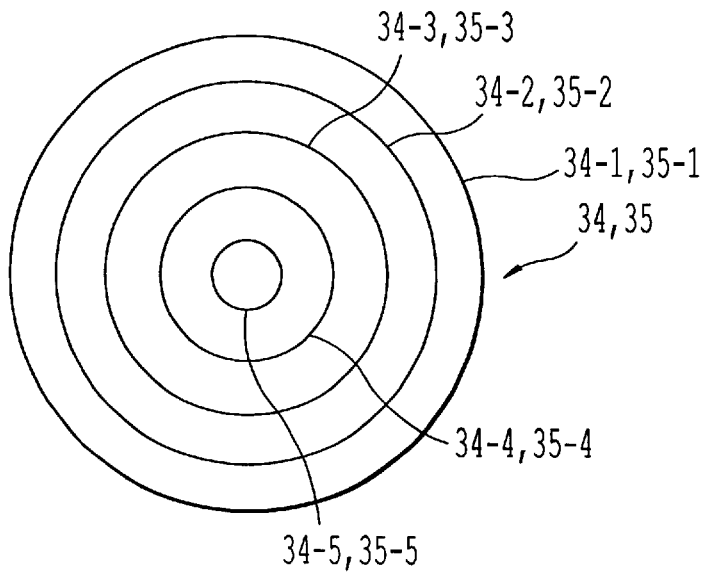
FIG. 20 is a top view of the multi-layer blank shown in FIG. 19A or 19B.
Figure 21:
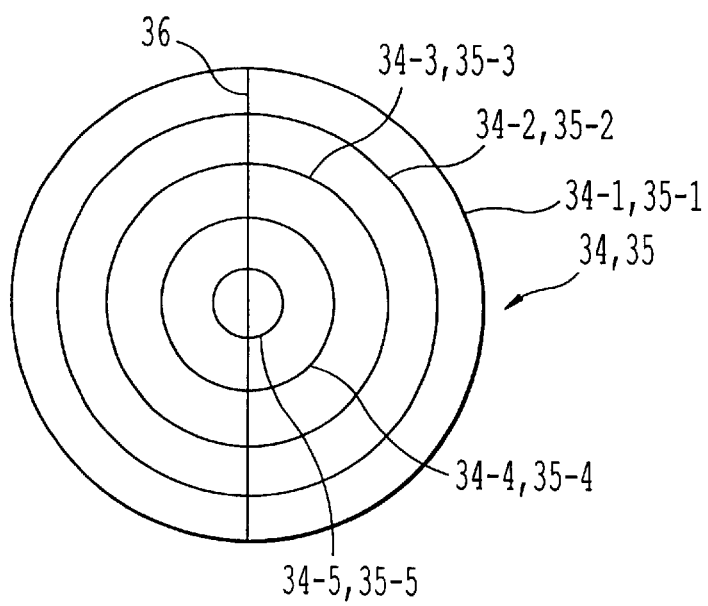
FIG. 21 is a top view of the multi-layer blank shown in FIG. 20 divided into two sections.
Figure 22:
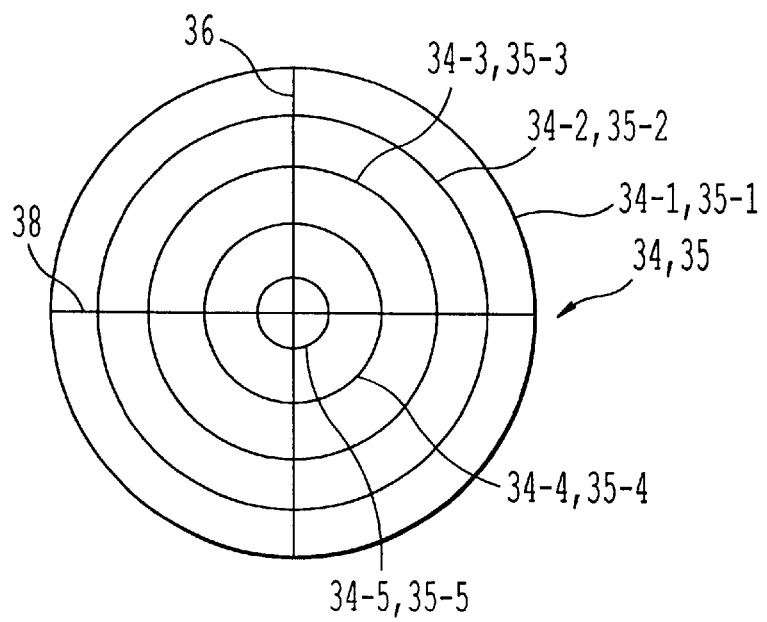
FIG. 22 is a top view of the multi-layer blank shown in FIG. 20 divided into four sections.
Figure 23:
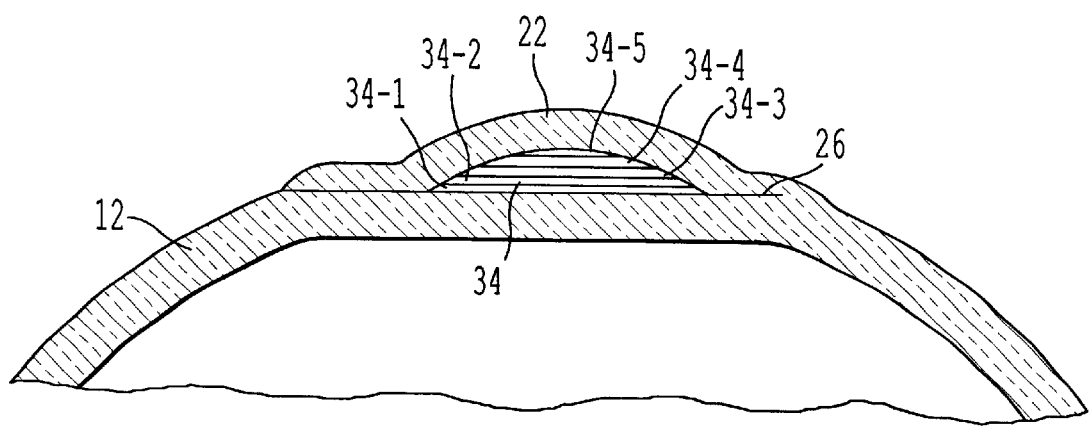
FIG. 23 is a side elevational view in section taken through the center of the eye showing the cornea and the flap-like portion reattached over the exposed surface of the cornea and a blank as shown in FIG. 19A being implanted therein.
Figure 24:
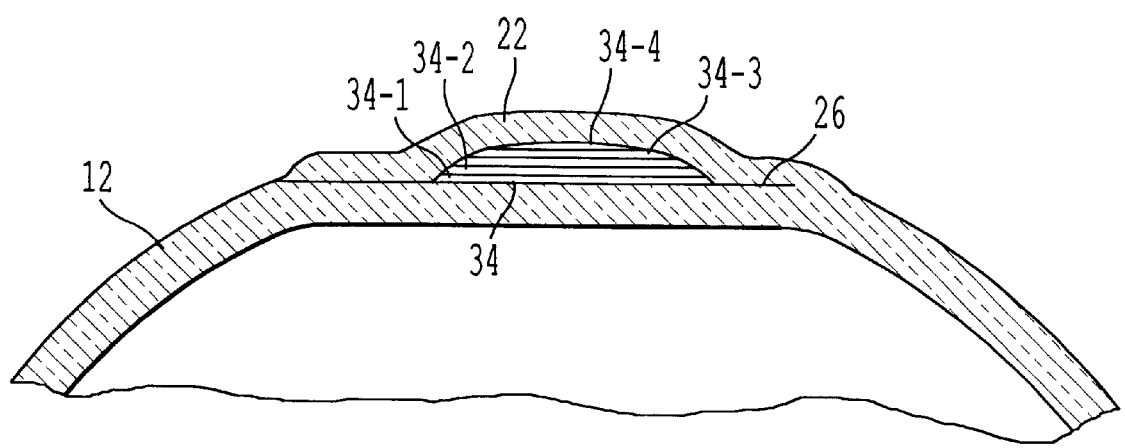
FIG. 24 is a side elevational view in section taken through the center of the eye showing the cornea and the flap-like portion reattached over the exposed surface of the cornea and a blank as shown in FIG. 19A being implanted therein, with one of the sections of the blank being removed.

It is further noted that the blank 18 can be configured as a multi-layer blank 34 as shown, for example in FIGS. 19A, 19B and 20. The multi-layer blanks 34 or 35 include, for example, sections 34-1 through 34-5, and sections 35-1 through 35-5, respectively, which can be separated from each other, as desired. The multi-layer blanks 34 and 35 each can include any number of layers having any suitable diameter, thickness and shape. Accordingly, the multi-layer blanks 34 or 35 can be implanted underneath a layer 22 in the cornea 12 in a manner similar to that discussed above with regard to blank 18. FIG. 23 illustrates an example of blank 34 implanted underneath a layer 22 of the cornea 12. When the layer 22 has been replaced and allowed to heal, the vision of the patient's eye can then be checked. If it is necessary to further adjust the curvature of the layer 22 to more accurately correct the vision disorder, one or more of the sections of the multi-layer blank 34 can be removed, as desired, to modify the corneal curvature as shown in FIG. 24. This removal of the appropriate sections can be performed by placing a small incision in the cornea 12 and removing the appropriate layer of the multi-layer blank 34. A similar process can be performed when blank 35 is implanted.

Alternatively, the layer 22 can be reseparated from the remainder form the cornea 12 so that appropriate layer of the multi-layer blank 34 can be removed. The layer 22 can then be replaced back over the remaining layers of the multi-layer blank 34 and permitted to heal. Also, the blanks 34 or 35 can be ablated, if desired, when the layer 22 is lifted to expose the blank 34 or 35. Furthermore, some or all of the layers 34-1 through 34-5, and 35-1 through 35-5 of the multi-layer blanks 34 and 35, respectively, may include the monomers or dyes as discussed above, so that those layers can be increased in volume or shrunk as desired, to further correct for the vision disorder without creating an incision in the cornea 12 or without reseparating the layer 22 from the cornea 12.

Figure 25:
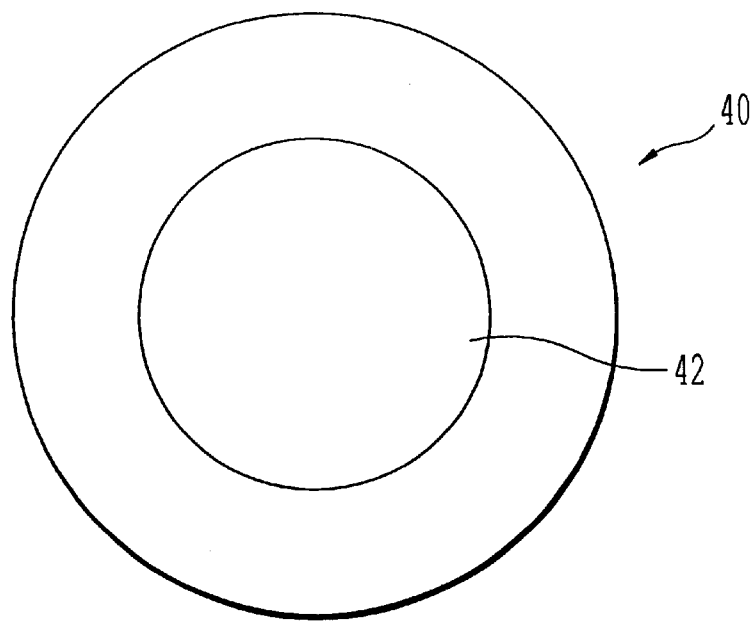
FIG. 25 is a top view of a ring-shaped blank according to another embodiment of the present invention.
Figure 26:
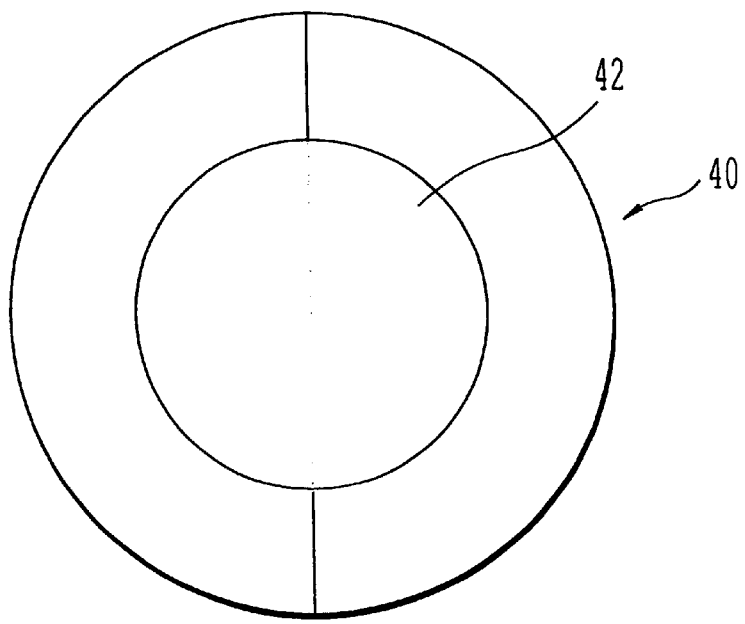
FIG. 26 is a top view of the ring-shaped blank shown in FIG. 23 divided into two sections.

As further shown in FIGS. 25 and 26, the multi-layer blanks 34 or 35 can be cut in half along line 36, in quarters along lines 36 and 38, or in any number of pieces, as desired. In this event, each of the layers 34-1 throughout 34-5, and 35-1 throughout 35-5, is either cut in half or quartered. Accordingly, the appropriate pieces of those layers 34-1 through 34-5, and 35-1 through 35-5, can be removed, as desired, to modify the curvature of the layer 22, as appropriate. Further portions of the layers 34-1 through 34-5, and 35-1 through 35-5, can be removed, as necessary, in the manners described above by reopening the layer 22 or through a small incision in the cornea 12, or alternatively, can be increased in volume or shrunk in the manners described above. Also, if desired, additional layers of the blanks 34 or 35 which were not initially implanted in the cornea 12 can be implanted through a small incision to change the curvature of the cornea 12.

In addition, as shown in FIG. 25, the blank can be a ring-shaped blank 40 having an opening 42 therein. The opening 42 can have any diameter ranging from a small hole to a diameter close to the outer diameter of the blank 40. As further shown in FIG. 26, the ring-shaped blank 40 can be separated, for example, into two halves 42-1 and 42-1, or in any number of pieces, as desired.

Figure 27:
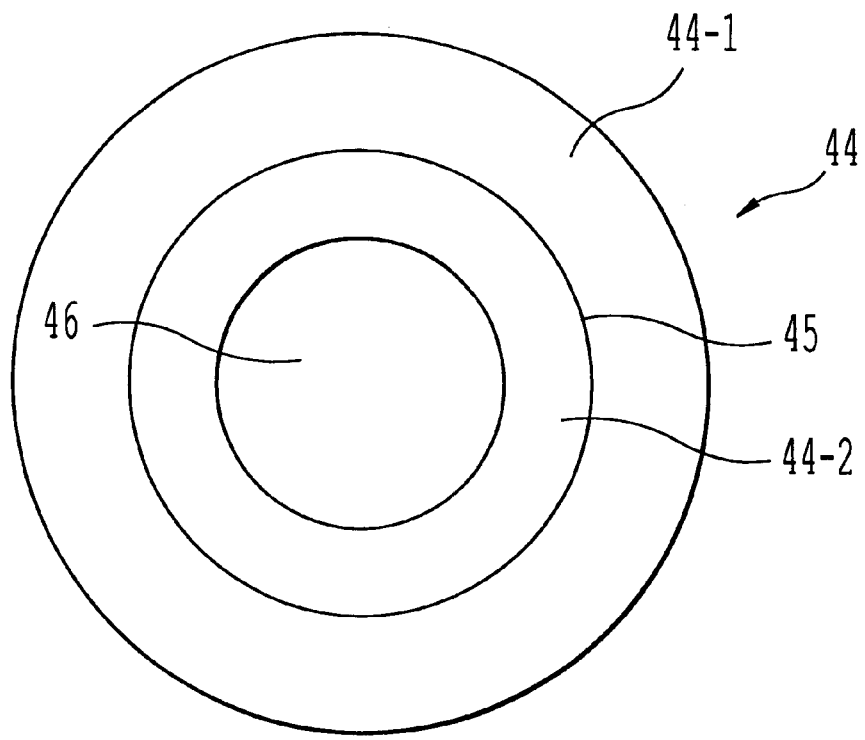
FIG. 27 is a top view of a multi-layer ring-shaped blank according to a further embodiment of the present invention.
Figure 28:
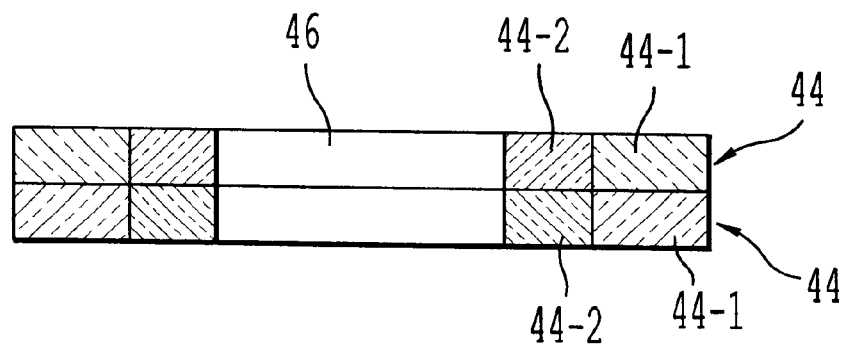
FIG. 28 is a cross-sectional view of the multi-layer ring-shaped blank shown in FIG. 27.
Figure 29:
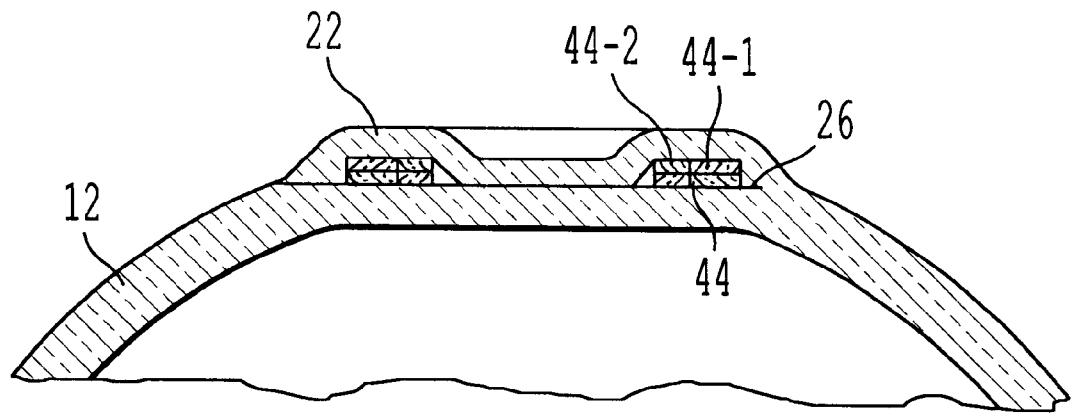
FIG. 29 is a side elevational view in section taken through the center of the eye showing the cornea and the flap-like portion reattached over the exposed surface of the cornea and a blank as shown in FIG. 28 being implanted therein.
Figure 30:
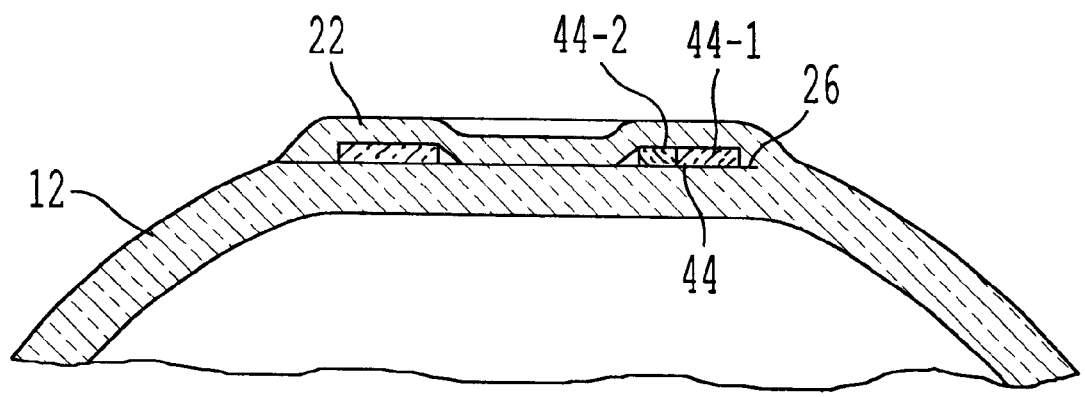
FIG. 30 is a side elevational view in section taken through the center of the eye showing the cornea and the flap-like portion reattached over the exposed surface of the cornea and a blank as shown in FIG. 28 being implanted therein, with one of the sections of the blank being removed.

Also, any of these types of ring-shaped blanks can be a multi-sectioned blank 44, as shown in FIGS. 27 and 28, having sections 44-1 and 44-2 and an opening 46 therein. As shown, section 44-2 fits inside the opening 45 of section 44-1 The multi-sectioned blanks 44 can also be stacked on top of each other to form a multi-layer blank 47 as shown in FIG. 28 specifically. As shown in FIG. 29, the multi-layer blank 47 can be implanted under the flap 22 in the cornea 12 to correct for high myopia. However, if the correction factor is too great, one of the layers 44, or one of the sections 44-1 or 44-2 of one of the layers 44, can be removed through a small incision in the cornea 12, so that only one section (e.g., section 44-2) of one layer 44 of the multi-layer blank remains under the flap 22, as shown in FIG. 30. This single section 44-2 can be used to correct for low myopia vision disorders. Also, as with blanks 34 and 35, further sections or layers 44 can be implanted in the cornea through a small incision to change the shape of the cornea as desired.

Figure 31:
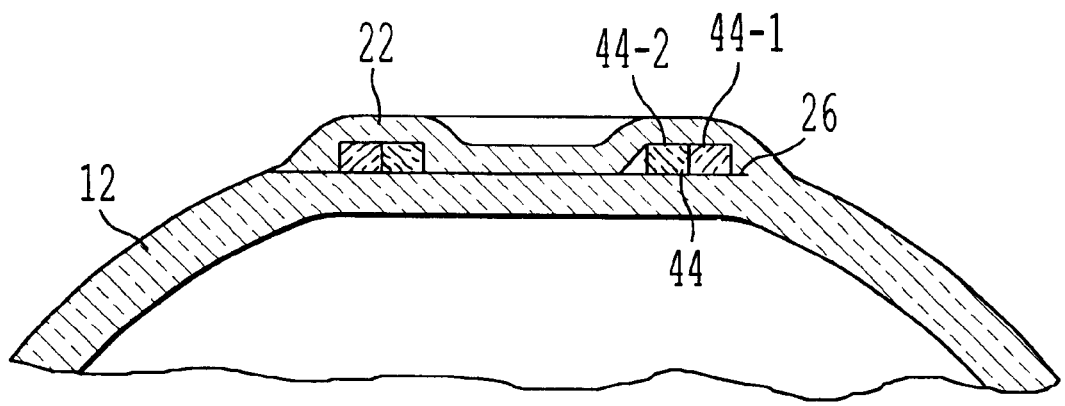
FIG. 31 is a side elevational view in section taken through the center of the eye showing the cornea and the flap-like portion reattached over the exposed surface of the cornea and one layer of the multi-layer blank as shown in FIG. 28 being implanted therein.
Figure 32:
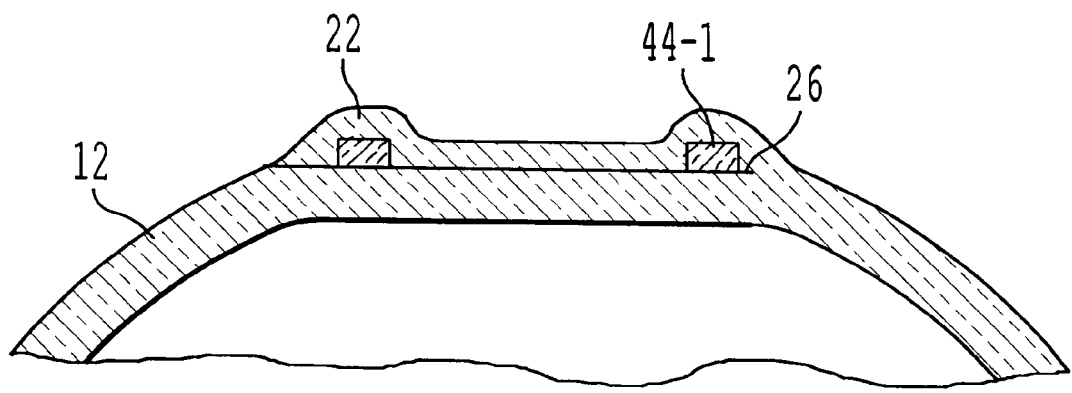
FIG. 32 is a side elevational view in section taken through the center of the eye showing the cornea and the flap-like portion reattached over the exposed surface of the cornea and one layer of the multi-layer blank as shown in FIG. 28 being implanted therein, with one of the sections of the blank being removed.

Also, as shown in FIG. 31, an entire single layer 44 having sections 44-1 and 44-2 can be implanted under the flap 22 in the cornea 12 to correct for a high myopia vision disorder. However, if it is determined that the correction factor is too great, one of the sections (e.g., section 44-2) can be removed from the cornea 12 through a small incision. In this event, the curvature of the flap 22 becomes less concave and thus, a lower correction power is achieved.

Figure 33:
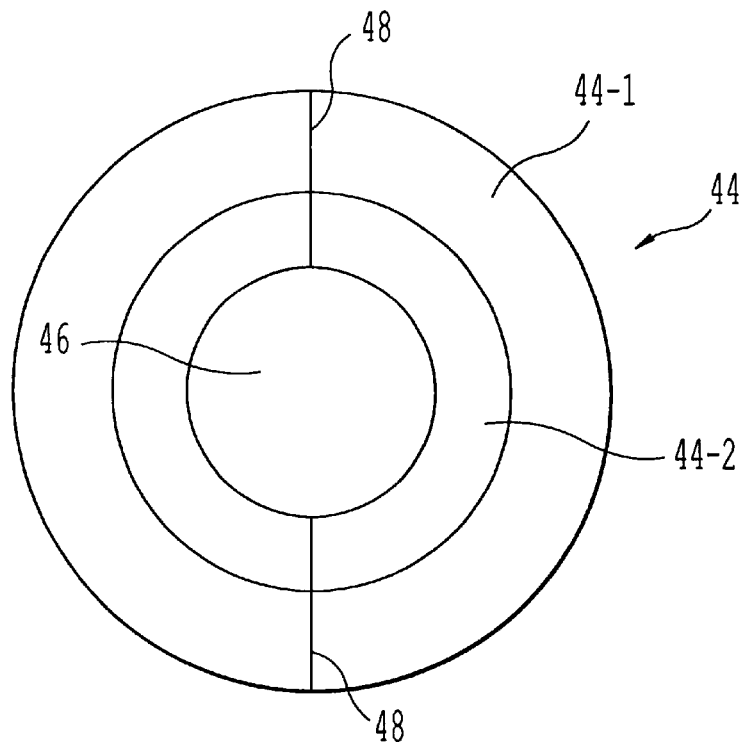
FIG. 33 is a top view of the multi-layer ring-shaped blank shown in FIG. 25 divided into two sections.
Figure 34:
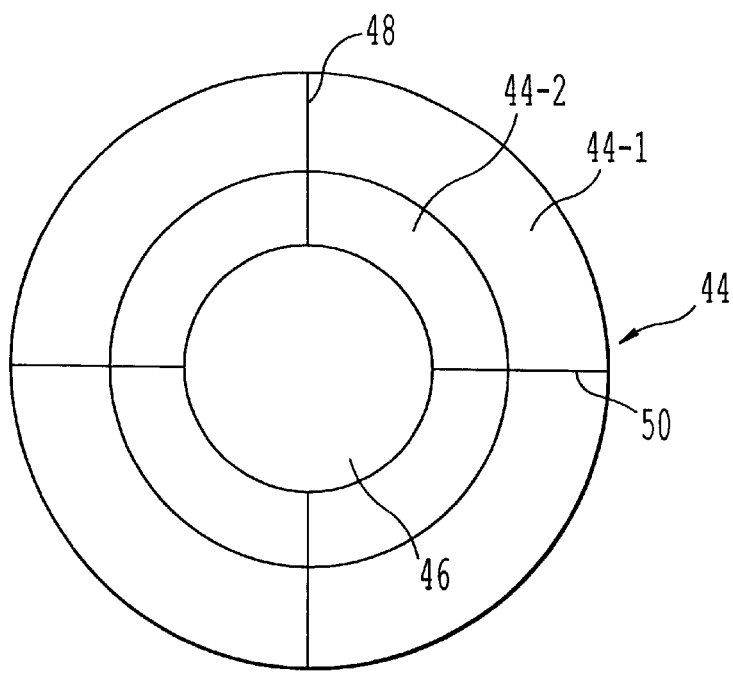
FIG. 34 is a top view of the multi-layer ring-shaped blank shown in FIG. 25 divided into four sections

As shown in FIGS. 33 and 34, multi-layer blanks 44 can also be divided into sections along lines 48 and 50. Also, any of these ring-shaped blanks 40 and 44 may include the monomers and dyes as discussed above so that the volume of the blanks 40 and 44 can be increased or shrunk, as appropriate, to change their respective thickness, and to also change the diameter of the openings 42 and 46 therein, to change the curvature of the layer 22 to correct for the vision disorder, as appropriate. Also, these types of blanks 40 and 44 may include the monomers or dyes as discussed above to create the increase or shrinkage in volume as desired to modify the curvature of the layer 22 as appropriate to correct for the vision disorder.

It is further noted that any of the blanks discussed above need not be positioned at the center of the eye 10 along the optical axis of the eye. Rather, the blanks can be positioned anywhere in the cornea 12, as deemed appropriate, to change the shape of the cornea 12 as necessary to correct the vision disorder. Furthermore, the flap-like layer 22 need not be at the center of the cornea 12, but rather, can be in any portion of the cornea 12 and can have any suitable shape, such as annular about the cornea 12 and so on.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A blank, adaptable for use in modifying the curvature of a patient's live cornea, comprising:

a first surface adaptable for placement directly on a surface of the patient's live cornea, and being conformable with the surface of the patients live cornea; and at least one of the following:

a first material which, when exposed to a first energy, is adapted to increase a volume of at least a portion of the blank substantially without ablation;

a second material which, when exposed to a second energy, is adapted to decrease a volume of at least a portion of the blank substantially without ablation;

a second surface adaptable to be exposed to laser light; and a third material whose properties permit light having a wavelength within the visible spectrum to pass therethrough and prevent at least some of said laser light from passing therethrough.

2. A blank as claimed in claim 1, further comprising:

a second surface, on a side opposite to said first surface; and wherein said first and second surfaces are spaced at a distance which provides a thickness at a perimeter of said blank which is sufficient to substantially prevent the laser beam from ablating the surface of the patient's live cornea located below said perimeter.

3. A blank as claimed in claim 1, wherein:
said first energy includes light within a first wavelength range.

4. A blank as claimed in claim 3, where:
said light is within a blue wavelength range or an ultraviolet wavelength range.

5. A blank as claimed in claim 1, wherein:
said second energy includes light within a second wavelength range.

6. A blank as claimed in claim 5, wherein:
said light includes infrared light.

7. A blank as claimed in claim 5, wherein:
said light includes continuous or pulsed laser light.

8. A blank as claimed in claim 1, wherein:
said second energy includes at least one of microwave energy, radio frequency energy and thermal energy.

9. A blank as claimed in claim 1, wherein:
said first material includes a monomer.

10. A blank as claimed in claim 1, wherein:
said second material includes a dye.

11. A method for modifying the curvature of a patient's live cornea, comprising:
placing a blank directly on a surface of the patient's live cornea, said blank being conformable with the substantially flat surface and including at least one of a first material and a second material; and
performing at least one of the following steps:
exposing said first material to a first energy to increase a volume of at least a portion of the blank without ablation; and
exposing said second material to a second energy to decrease a volume of at least a portion of the blank without ablation.

12. A method as claimed in claim 11, further comprising the steps of:
separating a layer of said cornea from a remainder of said cornea to create said surface; repositioning said layer over said blank after said placing step; and wherein said performing step is performed after said repositioning step.

13. A method as claimed in claim 11, wherein:
said first energy includes light within a first wavelength range.

14. A method as claimed in claim 11, wherein:
said light is within a blue wavelength range or an ultraviolet wavelength range.

15. A method as claimed in claim 11, wherein:
said second energy includes light within a second wavelength range.

16. A method as claimed in claim 15, wherein:
said light includes infrared light.

17. A method as claimed in claim 15, wherein:
said light includes continuous or pulsed laser light.

18. A method as claimed in claim 11, wherein:
said second energy includes at least one of microwave energy, radio frequency energy and thermal energy.

19. A method as claimed in claim 11, wherein:
said first material includes a monomer.

20. A method as claimed in claim 11, wherein:
said second material includes a dye.

21. A method for modifying the curvature of a patient's live cornea, comprising:
placing a blank directly on a surface of the patient's live cornea, said blank being conformable with the surface of the patient's live cornea and including at least one of a first material and a second material; and
performing at least one of the following steps:
exposing said first material to a first energy to increase a volume of at least a portion of the blank without ablation; and
exposing said second material to a second energy to decrease a volume of at least a portion of the blank without ablation.

22. A method as claimed in claim 21, further comprising the steps of:
separating a layer of said cornea from a remainder of said cornea to create said surface of the patient's line cornea;
repositioning said layer over said blank after said placing step; and
wherein said performing step is performed after said repositioning step.

23. A method as claimed in claim 21, wherein:
said first energy includes light within a first wavelength range.

24. A method as claimed in claim 21, wherein:
said light is within a blue wavelength range or an ultraviolet wavelength range.

25. A method as claimed in claim 21, wherein:
said second energy includes light within a second wavelength range.

26. A method as claimed in claim 25, wherein:
said light includes infrared light.

27. A method as claimed in claim 25, wherein:
said light includes continuous or pulsed laser light.

28. A method as claimed in claim 21, wherein: said second energy includes at least one of microwave energy, radio frequency energy and thermal energy.

29. A method as claimed in claim 21, wherein: said first material includes a monomer.

30. A method as claimed in claim 21, wherein: said second material includes a dye.

31. A blank, adaptable for use in modifying the curvature of a patient's live cornea, comprising:
a first surface adaptable for placement directly on a surface of the patient's live cornea, and being conformable with the substantially flat surface; and
at least one of the following:
a first material which, when exposed to a first energy, said first energy including light within a first wavelength range, is adapted to increase a volume of at least a portion of the blank substantially without ablation; and
a second material which, when exposed to a second energy, is adapted to decrease a volume of at least a portion of the blank substantially without ablation.

32. A blank as claimed in claim 31, further comprising:
a second surface adaptable to be exposed to laser light; and
a third material whose properties permit light having a wavelength within the visible spectrum to pass therethrough and prevent at least some of said laser light from passing therethrough.

33. A blank as claimed in claim 31, further comprising:
a second surface, on a side opposite to said first surface; and
wherein said first and second surfaces are spaced at a distance which provides a thickness at a perimeter of said blank which is sufficient to substantially prevent the laser beam from ablating the substantially flat surface of the patient's live cornea located below said perimeter.

34. A blank as claimed in claim 31, wherein:
said light is within a blue wavelength range or an ultraviolet wavelength range.

35. A blank as claimed in claim 31, wherein:
said second energy includes light within a second wavelength range.

36. A blank as claimed in claim 35, wherein:
said light includes infrared light.

37. A blank as claimed in claim 35, wherein:
said light includes continuous or pulsed laser light.

38. A blank as claimed in claim 31, wherein:
said second energy includes at least one of microwave energy, radio frequency energy and thermal energy.

39. A blank as claimed in claim 31, wherein:
said first material includes a monomer.

40. A blank as claimed in claim 31, wherein:
said second material includes a dye.

41. A blank, adaptable for use in modifying the curvature of a patient's live cornea, comprising:
a first surface adaptable for placement directly on a surface of the patient's live cornea, and being conformable with the substantially flat surface; and
at least one of the following:
a first material which, when exposed to a first energy, is adapted to increase a volume of at least a portion of the blank substantially without ablation; and
a second material which, when exposed to a second energy, is adapted to decrease a volume of at least a portion of the blank substantially without ablation;
wherein said first material includes a monomer.

42. A blank as claimed in claim 41, further comprising:
a second surface adaptable to be exposed to laser light; and
a third material whose properties permit light having a wavelength within the visible spectrum to pass therethrough and prevent at least some of said laser light from passing therethrough.

43. A blank as claimed in claim 41, further comprising:
a second surface, on a side opposite to said first surface; and
wherein said first and second surfaces are spaced at a distance which provides a thickness at a perimeter of said blank which is sufficient to substantially prevent the laser beam from ablating the substantially flat surface of the patient's live cornea located below said perimeter.

44. A blank as claimed in claim 41, wherein:
said first energy includes light within a first wavelength range.

45. A blank as claimed in claim 44, wherein:
said light is within a blue wavelength range or an ultraviolet wavelength range.

46. A blank as claimed in claim 41, wherein:
said second energy includes light within a second wavelength range.

47. A blank as claimed in claim 46, wherein:
said light includes infrared light.

48. A blank as claimed in claim 46, wherein:
said light includes continuous or pulsed laser light.

49. A blank as claimed in claim 41, wherein:
said second energy includes at least one of microwave energy, radio frequency energy and thermal energy.

50. A blank as claimed in claim 41, wherein:
said second material includes a dye.

51. A blank, adaptable for use in modifying the curvature of a patient's live cornea, comprising:
a first surface adaptable for placement directly on a surface of the patient's live cornea, and being conformable with the substantially flat surface; and
at least one of the following:
a first material which, when exposed to a first energy, is adapted to increase a volume of at least a portion of the blank substantially without ablation; and
a second material which, when exposed to a second energy, is adapted to decrease a volume of at least a portion of the blank substantially without ablation;
wherein said second material includes a dye.

52. A blank as claimed in claim 51, further comprising:
a second surface adaptable to be exposed to laser light; and
a third material whose properties permit light having a wavelength within the visible spectrum to pass therethrough and prevent at least some of said laser light from passing therethrough.

53. A blank as claimed in claim 51, further comprising:
a second surface, on a side opposite to said first surface; and
wherein said first and second surfaces are spaced at a distance which provides a thickness at a perimeter of said blank which is sufficient to substantially prevent the laser beam from ablating the substantially flat surface of the patient's live cornea located below said perimeter.

54. A blank as claimed in claim 51, wherein:
said first energy includes light within a first wavelength range.

55. A blank as claimed in claim 54, wherein:
said light is within a blue wavelength range or an ultraviolet wavelength range.

56. A blank as claimed in claim 51, wherein:
said second energy includes light within a second wavelength range.

57. A blank as claimed in claim 56, wherein:
said light includes infrared light.

58. A blank as claimed in claim 56, wherein:
said light includes continuous or pulsed laser light.

59. A blank as claimed in claim 51, wherein:
said second energy includes at least one of microwave energy, radio frequency energy and thermal energy.

60. A blank as claimed in claim 51, wherein:
said first material includes a monomer.

* * * * *